United States Patent [19]

Schindel

[11] 4,053,530

[45] Oct. 11, 1977

[54] CATALYZED FLUORINATION OF CHLOROCARBONS

[75] Inventor: Wesley Gerald Schindel, Pennsville, N.J.

[73] Assignee: E. I. Du Pont de Nemours and Company, Wilmington, Del.

[21] Appl. No.: 709,818

[22] Filed: July 29, 1976

[51] Int. Cl.$^2$ .......................................... C07C 17/10
[52] U.S. Cl. ................................................ 260/653.8
[58] Field of Search ................................... 260/653.8

[56] References Cited

U.S. PATENT DOCUMENTS

| 3,334,151 | 8/1967 | Okazaki | 260/653.8 |
| 3,480,667 | 11/1969 | Seigart et al. | 260/653.8 |
| 3,501,268 | 3/1970 | Laran et al. | 423/483 |

Primary Examiner—C. Davis

[57] ABSTRACT

Described is the production of chlorofluorocarbons, particularly trichlorofluoromethane, by reaction between chlorocarbons, e.g., carbon tetrachloride, and ammonium bifluoride at around 300°–550° C in the presence of certain catalysts, e.g., an alkaline earth metal fluoride or ferric fluoride, calcium fluoride being preferred.

10 Claims, 1 Drawing Figure

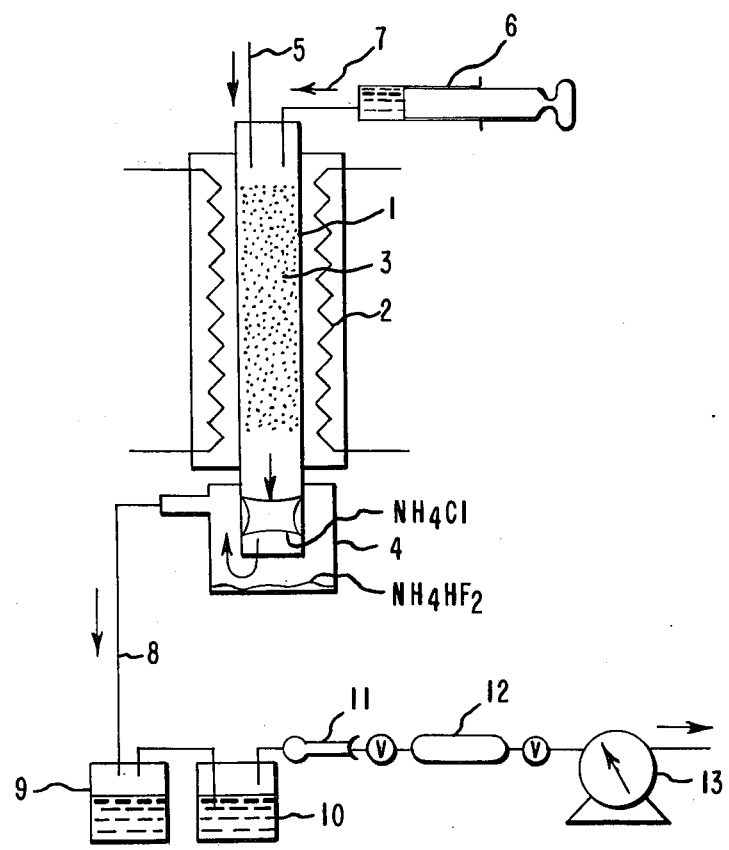

CATALYZED FLUORINATION OF CHLOROCARBONS

BACKGROUND OF THE INVENTION

1. Field of the Invention

This invention relates to the catalyzed production of chlorofluorocarbons, for example, trichlorofluoromethane, from chlorocarbons and ammonium bifluoride.

2. Prior Art

U.S. Pat. No. 3,501,268 shows the equation

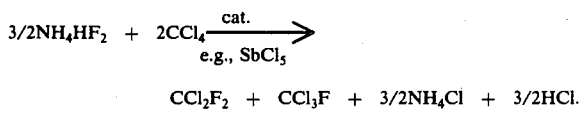

$$CCl_2F_2 + CCl_3F + 3/2NH_4Cl + 3/2HCl.$$

This reaction is carried out in a batch process over about 2⅔ hours in Example 7 of the patent.

U.S. Pat. No. 3,696,150 shows the fluorination of reactive organic compounds such as triphenylchloromethane, ethyl chloroformate, acetyl bromide, etc., with $NH_4F$ or $NH_4HF_2$.

SUMMARY OF THE INVENTION

This invention is the production of valuable chlorofluorocarbons, e.g., trichlorofluoromethane, by catalyzed reaction between carbon tetrachloride or chloroform and ammonium bifluoride, calcium fluoride being the preferred catalyst. The reaction with carbon tetrachloride might be described according to the equation:

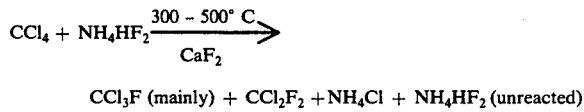

$CCl_3F$ (mainly) + $CCl_2F_2$ + $NH_4Cl$ + $NH_4HF_2$ (unreacted)

DESCRIPTION OF THE DRAWING

The drawing described more fully below is a schematic representation of apparatus in which the reaction constituting the present invention may be carried out.

DESCRIPTION OF THE INVENTION

In accordance with the present invention, it has been found that certain chlorocarbons, e.g., carbon tetrachloride, chloroform, can be fluorinated to useful chlorofluorocarbons, e.g., trichlorofluoromethane, dichlorofluoromethane, by ammonium bifluoride in the presence of selected catalysts at elevated temperature. It is merely necessary to contact the reactants briefly under the conditions noted for the reaction to occur.

Catalysts useful in the reaction include the Group IIa fluorides, i.e., those of calcium, magnesium, strontium and barium, as well as ferric cluoride, anhydrous chromic fluoride and chromic phosphate. Mixtures of these catalysts can also be used, e.g., the Group IIa fluorides and ferric fluoride are operable in mixture with each other.

The fluorides of the Group IIa metals, Fe(III) and Cr(III) may be prepared in place from the corresponding chlorides by vapor phase reaction with HF or with $NH_4HF_2$. "Chromic fluoride" as used here means the product resulting from reaction of chromic chloride with $NH_4HF_2$ following dehydration on heating to 300° C under vacuum as taught in U.S. Pat. No. 3,600,450. X-ray diffraction shows that most of the chlorine originally present is replaced by fluorine.

The catalysts are preferably employed alone in the form of pellets. Optionally, they may be supported on other materials such as aluminum fluoride or carbon. Aluminum oxide support is probably converted to aluminum fluoride on fluoride pretreatment as described in examples. Precipitated calcium fluoride in the form of pellets is preferred. Ground fluorospar, a natural calcium fluoride, is operable and falls within the invention. Vapor-phase reaction over catalysts as described is contemplated.

Temperature in the reaction is not strictly critical, and may vary somewhat with the chlorocarbon and the catalyst. In general, however, temperatures between about 300° and 550° C are operable.

The principal fluorinated product of the present reaction with carbon tetrachloride is $CFCl_3$ but other products, e.g., $CCl_2F_2$, are formed as well, as is shown in the tables. When chloroform is a reactant, $CHCl_2F$ is the main product formed.

When carbon tetrachloride and ammonium bifluoride are reacted in molar ratio to produce mainly trichlorofluoromethane, one mole of hydrogen fluoride is produced, which can usefully be recycled to produce more trichlorofluoromethane. Simple cofeeding of hydrogen fluoride along with ammonium bifluoride is also operable.

Vapor-phase reactions illustrating the invention were carried out in a laboratory-size, fixed catalyst bed reactor and associated equipment as shown in the Figure. This figure shows reactor 1, a 2.5-cm inside diameter Inconel nickel alloy pipe heated over a length of 41 cm by means of electric heaters 2, which contains catalyst 3. The downstream end of the reactor terminates in trap 4 and tubulation leading to a purification, sampling and gas measuring train. Chlorocarbon is metered, for example, by means of a pump not shown, through pipeline 5 into reactor 1. Molten ammonium bifluoride (melting point ca. 126° C) is simultaneously metered into reactor 1 by means of motor driven pump 6 (motor drive not shown) through line 7. The bifluoride is maintained molten by heating means (not shown) which are applied to pump 6 and line 7.

The chlorocarbon and ammonium bifluoride reactants pass as vapors through catalyst 3 where they react at least in part to form products. The product stream after leaving catalyst 3 passes through trap 4 where separately ammonium chloride and unreacted ammonium bifluoride are deposited as shown. Gaseous products pass, via line 8, over water in scrubber 9, which removes possible water-soluble materials, through 10 wt. percent aqueous KOH in scrubber 10, which removes remaining acids, thence through drying tube 11 containing anhydrous calcium sulfate which dries the gas stream. Samples removed from the stream in sample bulb 12 are analyzed from time to time by vapor phase chromatography using a DC-200 silicone column. The volume of dried gas, consisting essentially of organic products, is measured by means of the gas meter 13. In practice, scrubbers 9 and 10 were normally chilled by means of ice water (not shown) to prevent the passage of easily condensible materials into the downstream elements of the train. Organic materials condensed in scrubbers 9 and 10 were recovered and similarly analyzed by vapor-phase chromatography.

Temperatures in the catalyst bed were monitored by means of thermocouples not shown and are reported in tables following as a range of temperatures from the lowest to the highest observed.

The ideal gas law was employed in the calculation of the mole flow rate of gas passing through gas meter 13. This value divided by the number of moles of chlorocarbon charged during the same period of time yielded the mole fraction of chlorocarbon converted to gas. Analysis values for the components of the gas and the condensed organic product were arithmetically combined to produce values expressing in mole percent the total conversion of chlorocarbon into the various products. This was done by multiplying the analysis values in mole percent derived from the gas, by the mole fraction of chlorocarbon converted to gas and adding this product to the product of similar analysis values derived from the condensed organic product multiplied by the complement of the mole fraction of chlorocarbon converted to gas. In the tables of experimental results given below, these values, representing the composition of the total products of reaction condensed or not, are shown in columns labelled "Products (Mol. %)."

Space velocity hr$^{-1}$ as used in the same tables means the calculated hypothetical volume of chlorocarbon and $NH_4HF_2$ gas feed at 0° C and 1 atm per hour divided by the bulk volume of the catalyst. $NH_4HF_2$ was assumed to dissociate into three molecules, i.e., one mole of $NH_3$ and two moles of HF.

Chlorocarbon utilization (mole %) as used in the tables is arrived at by substracting the sum of the precentages of $CClF_3$, $CHF_3$ (not distinguishable from $CO_2$ and $CClF_3$ by chromatographic analysis), $CCl_2=CCl_2$ and $CCl_3CCl_3$, from 100. The value is a measure of formation of useful one-carbon products which either in themselves are useful or could be converted into useful products by recycling through the reactor.

product stream small amounts of chloroform and related chlorofluorocarbons.

There follow some examples illustrating the invention in detail, Example 1 serving merely as a control. The reactor of the Figure was used in all examples.

EXAMPLE 1

Control

In a run made in the apparatus described above, it was found that at 350°-400° C only traces of $CCl_3F$ were formed when $CCl_4$ and $NH_4HF_2$ were passed through the described reactor in the absence of catalyst.

It was also found by X-ray diffraction and wet analysis of calcium fluoride catalyst from runs like those in Examples 2-7 that there were only traces of chlorine in such used catalysts. The result shows that the calcium fluoride was acting catalytically and not as a fluorinating agent.

EXAMPLES 2-7

Carbon Tetrachloride and Ammonium Bifluoride with Calcium Fluoride Catalysts A number of runs were carried out passing ammonium bifluoride and carbon tetrachloride through catalysts consisting of precipitated calcium fluoride pellets (Examples 2 and 3), calcium fluoride on carbon (Example 4), calcium fluoride on aluminum fluoride (ex $Al_2O_3$) (Examples 5 and 6) and ground acid grade fluorspar suitable for the manufacture of HF (Example 7).

Liquid $CCl_4$ and molten $NH_4HF_2$ were injected cocurrently downwardly through the hot catalyst as indicated in the Figure, $NH_4Cl$ depositing on the wall of the pipe and unreacted $NH_4HF_2$ passing through to deposit in the trap. Conditions (temperature, mole ratio, and space velocity) and products are shown in Table I.

TABLE I

| | CARBON TETRACHLORIDE REACTION CATALYSIS BY CALCIUM FLUORIDE PELLETS | | | | | |
|---|---|---|---|---|---|---|
| | Precipitated $CaF_2$ Pellets | | $CaF_2$ (17 wt. %) on Carbon[1] | $CaF_2$ (27 wt. %) on $AlF_3$[2] | | Acid Grade Fluorspar |
| Conditions: | Ex. 2 | Ex. 3 | 4 | Ex. 5 | Ex. 6 | Ex. 7 |
| Temp. (° C) | 390 – 465 | 395 – 480 | 345 – 425 | 385 – 490 | 375 – 480 | 330 – 450 |
| $NH_4HF_2/CCl_4$ (mole) | 1.7 | 1.7 | 1.4 | 1.3 | 1.3 | 1.4 |
| Space Velocity hr.$^{-1}$ | 345 | 345 | 300 | 305 | 303 | 300 |
| Products (mol. %): | | | | | | |
| $CClF_3$, $CHF_3$, $CO_2$ | — | — | 0.03 | 1.9 | 0.27 | 0.03 |
| $CHClF_2$ | 0.09 | — | 0.07 | — | 0.00 | 0.12 |
| $CCl_2F_2$ | 3.8 | 3.1 | 0.04 | 0.78 | 0.55 | 0.87 |
| $CHCl_2F$ | 0.16 | 0.66 | 0.50 | 0.00 | 0.04 | 0.08 |
| $CCl_3F$ | 76.1 | 72.7 | 13.9 | 20.9 | 26.0 | 19.8 |
| $CHCl_3$ | 0.38 | 1.3 | 17.8 | 1.9 | 2.1 | 1.1 |
| $CCl_4$ | 17.4 | 17.6 | 56.3 | 65.8 | 61.1 | 70.3 |
| $CCl_2=CCl_2$ | 1.8 | 3.8 | 9.7 | 8.3 | 8.3 | 6.6 |
| $CCl_3CCl_3$ | 0.05 | 0.05 | 0.70 | 0.17 | 0.25 | 0.31 |
| Unknown | — | — | 0.57 | 0.30 | 1.05 | — |
| Other Results: | | | | | | |
| Chlorocarbon Utilization (mol. %) | 98.2 | 96.1 | 89.6 | 89.6 | 91.2 | 93.0 |

[1]Wood charcoal particle size 1.7 - 2.4 mm. impregnated with aqueous $CaCl_2$, dried and treated with HF while bringing the catalyst to reaction temperature.
[2]$Al_2O_3$ impregnated with aqueous $CaCl_2$ and treated as under [1] above.

Products are regarded as useful for reasons of both chemical convertibility into saleable materials and for intrinsic economic value. For the purposes of this description, the following components of product streams are regarded as useful: $CHClF_2$, $CCl_2F_2$, $CHCl_2F$, $CHCl_3$ and $CCl_4$.

Ammonium bifluoride is observed to reduce small amounts of carbon tetrachloride thus to produce in the

EXAMPLE 8

Chloroform and Ammonium Bifluoride with Calcium Fluoride Catalyst

The experiment described in Table II demonstrates that chloroform undergoes reaction with ammonium bifluoride with high utilization of chlorocarbon over calcium fluoride pellets as in Examples 2 and 2. Recycle and/or lesser space velocity can be employed to increase the conversion of chloroform.

The appearance of small amounts of $CCl_4$ and related $CCl_3F$ among the products may result from chlorination of chloroform by chlorine atoms resulting from radical reactions of the kind which also produced small amounts of $CCl_2=CCl_2$.

TABLE II
CHLOROFORM REACTION CATALYSIS BY PRECIPITATED CALCIUM FLUORIDE PELLETS

| Conditions: | |
|---|---|
| Temp. (° C) | 360 – 435 |
| $NH_4HF_2/CHCl_3$ (mole) | 1.2 |
| Space Velocity hr.$^{-1}$ | 260 |
| Products (mol. %): | |
| $CClF_3$, $CHF_3$, $CO_2$ | — |
| $CHClF_2$ | 0.52 |
| $CHCl_2F$ | 14.5 |
| $CCl_3F$ | 0.10 |
| $CHCl_3$ | 81.4 |
| $CCl_4$ | 0.23 |
| $CCl_2=CCl_2$ | 0.05 |
| Unknown | 3.2 |
| Other Results: | |
| Chlorocarbon Utilization (mol. %) | ~100 |

EXAMPLES 9 – 12

Carbon Tetrachloride and Ammonium Bifluoride with Ferric Fluoride Catalyst

Table III describes experiments demonstrating catalysis of the ammonium bifluoride-carbon tetrachloride reaction by means of ferric fluoride ($FeF_3$) pellets (Examples 9 and 10) and ferric fluoride supported on calcium fluoride (Examples 11 and 12), and in one case (Example 10), the cofeeding of HF as a second source of fluorine.

The results demonstrate good utilization of chlorocarbon in reactions catalyzed by ferric fluoride in unsupported pellets and by calcium fluoride-supported ferric chloride pretreated with ammonium bifluoride, presumably to produce ferric fluoride.

HF pretreatment of calcium fluoride pellets impregnated with ferric chloride produced an operable catalyst which produced rather large amounts of $CCl_2=CCl_2$ as compared with similar catalyst prepared by pretreatment with ammoniun bifluoride. Optimization of conditions using HF pretreated catalysts might lie in the direction of slightly lower temperatures.

TABLE III
CARBON TETRACHLORIDE REACTION CATALYSIS BY FERRIC FLUORIDE AND FERRIC FLUORIDE DOPED CALCIUM FLUORIDE

| | $FeF_3$ Pellets | | $FeF_3$ (7.2 wt.%) on ppt'd $CaF_2$ Pellets | |
|---|---|---|---|---|
| Conditions: | Ex. 9 | Ex. 10 | Ex. 11 | Ex. 12 |
| Temp. (° C) | 320 – 430 | 350 – 420$^{(1)}$ | 380 – 480$^{(2)}$ | 380 – 475$^{(3)}$ |
| $NH_4HF_2/CCl_4$ (mole) | 1.3 | 1.1 | 1.15 | 1.3 |
| Space Velocity hr.$^{-1}$ | 305 | 325 | 260 | 305 |
| Products (mol. %): | | | | |
| $CClF_3$, $CHF_3$, $CO_2$ | 2.6 | 0.01 | 0.00 | 2.5 |
| $CHClF_2$ | 0.30 | 0.02 | 0.12 | 1.0 |
| $CCl_2F_2$ | 6.3 | 0.31 | 0.86 | 16.0 |
| $CHCl_2F$ | 1.0 | 0.26 | 0.08 | 1.7 |
| $CCl_3F$ | 73.8 | 33.0 | 19.8 | 25.7 |
| $CHCl_3$ | 0.61 | 3.0 | 1.1 | 3.3 |
| $CCl_4$ | 10.8 | 44.8 | 70.3 | 15.4 |
| $CCl_2=CCl_2$ | 4.4 | 16.7 | 6.6 | 33.0 |
| $CCl_3CCl_3$ | 0.01 | 0.12 | 0.31 | 0.03 |
| Unknown | — | — | — | — |
| Other Results: | | | | |
| Chlorocarbon Utilization (mol. %) | 93.0 | 83.18 | 93.1 | 64.5 |

$^{(1)}$0.93 mol. HF per mole $NH_4HF_2$ was cofed.
$^{(2)}$10 wt.% $FeCl_3$ on $CaF_2$ pretreated with $NH_4HF_2$ at reaction temp.
$^{(3)}$10 wt. % $FeCl_3$ on $CaF_2$ pretreated with HF while heating to reaction temp.

EXAMPLES 13–16

Carbon Tetrachloride and Ammonium Bifluoride with Various Catalysts

A number of runs were made demonstrating the use of the fluorides of magnesium (Example 13), barium (Examples 14 and 15) and strontium (Example 16) in the ammonium bifluoride carbon tetrachloride reaction. Results are shown in Table IV.

TABLE IV
CARBON TETRACHLORIDE REACTION CATALYSIS BY Mg, Ba AND Sr DIFLUORIDES

| | $MgF_2$ Pellets | $BaF_2$ Pellets | | $SrF_2$ Pellets |
|---|---|---|---|---|
| Conditions: | Ex. 13 | Ex. | Ex. 15 | Ex. 16 |
| Temp. (° C) | 390 – 465 | 370 – 470 | 405 – 480 | 360 – 440 |
| $NH_4HF_2/CCl_4$ (mole) | 1.7 | 1.2 | 1.4 | 1.3 |
| Space Velocity hr.$^{-1}$ | 345 | 260 | 300 | 255 |
| Products (mol. %): | | | | |
| $CClF_3$, $CHF_3$, $CO_2$ | — | — | — | — |
| $CHClF_2$ | 0.10 | — | — | — |
| $CCl_2F_2$ | 2.90 | 0.69 | 0.37 | 0.06 |
| $CHCl_2F$ | 0.18 | 0.05 | — | 0.02 |
| $CCl_3F$ | 45.3 | 13.3 | 6.7 | 28.9 |
| $CHCl_3$ | 1.2 | 1.9 | 3.7 | 0.67 |
| $CCl_4$ | 47.3 | 65.9 | 68.8 | 66.2 |
| $CCl_2=CCl_2$ | 2.7 | 14.0 | 16.4 | 3.3 |
| $CCl_3CCl_3$ | 0.28 | 3.3 | 3.1 | 0.17 |
| Unknown | 0.09 | 0.59 | 0.7 | — |
| Other Results: | | | | |

TABLE IV-continued
CARBON TETRACHLORIDE REACTION CATALYSIS BY Mg, Ba AND Sr DIFLUORIDES

|  | $MgF_2$ Pellets | $BaF_2$ Pellets | $SrF_2$ Pellets |
|---|---|---|---|
| Chlorocarbon Utilization (mol. %) | 97.0 | 82.7 | 80.5 | 96.5 |

Other catalysts were found to be operable. For example, chromic phosphate, $CrPO_4$, catalyzed the reaction of $NH_4HF_2$ with $CCl_4$ to produce a product stream containing 20–25 mole percent $CCl_3F$. Chromic chloride prepared by dehydration of the hydrous form according to U.S. Pat. No. 3,600,450 was catalytically active producing, presumably following conversion to $CrF_3$, variable concentrations of $CCl_3F$ in the product stream up to about 70 mole percent.

I claim:

1. The process of fluorinating carbon tetrachloride or chloroform which comprises reacting, at a temperature of around 300°–550° C. and in vapor phase,
   at least one of the same with ammonium bifluoride
   in the presence of at least one catalyst of the group consisting of calcium, magnesium, barium, strontium, ferric and chromic fluorides and chromic phosphate.

2. The process of claim 1 wherein carbon tetrachloride and ammonium bifluoride are reacted together in the presence of calcium fluoride.

3. The process of claim 1 wherein carbon tetrachloride and ammonium bifluoride are reacted together in the presence of ferric fluoride.

4. The process of claim 1 wherein carbon tetrachloride and ammonium bifluoride are reacted together in the presence of magnesium fluoride.

5. The process of claim 1 wherein carbon tetrachloride and ammonium bifluoride are reacted together in the presence of barium fluoride.

6. The process of claim 1 wherein carbon tetrachloride and ammonium bifluoride are reacted together in the presence of strontium fluoride.

7. The process of claim 1 wherein carbon tetrachloride and ammonium bifluoride are reacted together in the presence of chromic fluoride.

8. The process of claim 1 wherein carbon tetrachloride and ammonium bifluoride are reacted together in the presence of chromic phosphate.

9. The process of claim 1 wherein carbon tetrachlorine and ammonium bifluoride are reacted together in the presence of calcium fluoride to form trichlorofluoromethane.

10. The process of claim 1 wherein chloroform and ammonium bifluoride are reacted together in the presence of calcium fluoride to form dichlorofluoromethane.

* * * * *